(12) United States Patent
De Silva

(10) Patent No.: US 10,124,087 B2
(45) Date of Patent: Nov. 13, 2018

(54) DETACHABLE COUPLING FOR CATHETER

(75) Inventor: Praveen De Silva, Irvine, CA (US)

(73) Assignee: COVIDIEN LP, Mansfield, MA (US)

( * ) Notice: Subject to any disclaimer, the term of this patent is extended or adjusted under 35 U.S.C. 154(b) by 598 days.

(21) Appl. No.: 13/526,611

(22) Filed: Jun. 19, 2012

(65) Prior Publication Data
US 2013/0338643 A1   Dec. 19, 2013

(51) Int. Cl.
*A61L 29/10* (2006.01)
*C08L 71/02* (2006.01)
(Continued)

(52) U.S. Cl.
CPC ........ *A61L 29/10* (2013.01); *A61B 17/12031* (2013.01); *A61B 17/12113* (2013.01);
(Continued)

(58) Field of Classification Search
CPC .......... A61M 25/0069; A61M 25/0045; A61M 39/10; A61M 39/12; A61M 25/0014; A61M 2039/1077; A61M 2025/0046; A61M 39/165; A61L 29/10; C08L 71/02; C08L 77/00; C08L 23/06; B29C 66/1142; B29C 66/5344; B29C 66/949; B29C 66/5229; B29C 66/723; B29C 66/712; B29C 66/1122; B29C 65/02; B29C 65/76; B29C 66/91411; B29C 66/91413; B29C 66/52298; B29C 66/73791; B29C 66/919; B29C 65/48; B29C 65/4895; B29C 65/10; B29C 65/16; B29C 66/71; A61B 17/12186; A61B 17/12031; A61B 17/12195;
(Continued)

(56) References Cited

U.S. PATENT DOCUMENTS 2,326,159 A   8/1943   Mendel
3,058,473 A   10/1962   Whitehead
(Continued)

FOREIGN PATENT DOCUMENTS

CN   102186526 A   9/2011
DE   1875646 U    7/1963
(Continued)

OTHER PUBLICATIONS

European Search Report dated Sep. 23, 2013 from corresponding European Application No. 13169745.0. (5 pgs.).
(Continued)

*Primary Examiner* — Lauren P Farrar
(74) *Attorney, Agent, or Firm* — Shumaker & Sieffert, P.A.

(57) ABSTRACT

A microcatheter comprising an elongate flexible tubular body, a tip body and a coupling is disclosed. The elongate flexible tubular body has a proximal end, a distal end and at least one lumen extending axially therethrough. The tip body has a proximal end and a distal end and a lumen extending axially therethrough. The coupling covers a portion of both the tubular body and tip body and is made from a first material and a second material, where the first material is different from the second material. The first material is compatible with an outermost layer of the tubular body and an outermost layer of the tip body, and the second material is configured to form a detachable bond with at least one of the tubular body and the tip body.

28 Claims, 7 Drawing Sheets

(51) Int. Cl.
*C08L 77/00* (2006.01)
*C08L 23/06* (2006.01)
*B29C 65/00* (2006.01)
*B29C 65/76* (2006.01)
*A61B 17/12* (2006.01)
*A61M 25/00* (2006.01)
*A61B 90/00* (2016.01)
*B29C 65/10* (2006.01)
*B29C 65/48* (2006.01)
*B29C 65/18* (2006.01)
*B29C 65/02* (2006.01)
*A61B 17/00* (2006.01)
*B29C 65/16* (2006.01)
*B29L 31/00* (2006.01)

(52) U.S. Cl.
CPC .. *A61B 17/12186* (2013.01); *A61B 17/12195* (2013.01); *A61M 25/0009* (2013.01); *A61M 25/0045* (2013.01); *A61M 25/0069* (2013.01); *B29C 65/02* (2013.01); *B29C 65/76* (2013.01); *B29C 66/1122* (2013.01); *B29C 66/1142* (2013.01); *B29C 66/5229* (2013.01); *B29C 66/5344* (2013.01); *B29C 66/712* (2013.01); *B29C 66/723* (2013.01); *B29C 66/949* (2013.01); *C08L 23/06* (2013.01); *C08L 71/02* (2013.01); *C08L 77/00* (2013.01); *A61B 2017/00004* (2013.01); *A61B 2017/12054* (2013.01); *A61B 2090/037* (2016.02); *A61L 2420/08* (2013.01); *A61M 25/007* (2013.01); *A61M 2025/0042* (2013.01); *A61M 2025/0046* (2013.01); *A61M 2025/0057* (2013.01); *B29C 65/10* (2013.01); *B29C 65/16* (2013.01); *B29C 65/18* (2013.01); *B29C 65/48* (2013.01); *B29C 65/4895* (2013.01); *B29C 66/52298* (2013.01); *B29C 66/71* (2013.01); *B29C 66/73791* (2013.01); *B29C 66/919* (2013.01); *B29C 66/91411* (2013.01); *B29C 66/91413* (2013.01); *B29K 2995/0056* (2013.01); *B29L 2031/7542* (2013.01); *F04C 2270/041* (2013.01); *Y10T 156/10* (2015.01)

(58) Field of Classification Search
CPC ......... A61B 2090/037; F04C 2270/041; Y10T 156/10; B29K 2995/0056; B29L 2031/7542
USPC .................. 604/538, 535, 539, 533, 534
See application file for complete search history.

(56) References Cited

U.S. PATENT DOCUMENTS

| | | |
|---|---|---|
| 3,656,485 A | 4/1972 | Robertson |
| 3,656,486 A | 4/1972 | Robertson |
| 3,674,014 A | 7/1972 | Tillander |
| 3,977,409 A | 8/1976 | Brendling |
| 4,346,712 A | 8/1982 | Handa et al. |
| 4,364,392 A | 12/1982 | Strother et al. |
| 4,385,631 A | 5/1983 | Uthmann |
| 4,395,806 A | 8/1983 | Wonder et al. |
| 4,402,319 A | 9/1983 | Handa et al. |
| 4,545,367 A | 10/1985 | Tucci |
| 4,631,188 A | 12/1986 | Stoy et al. |
| 4,655,762 A * | 4/1987 | Rogers .............. A61M 39/16 128/912 |
| 4,663,358 A | 5/1987 | Hyon et al. |
| 4,698,056 A | 10/1987 | Ciannella |
| 4,739,768 A | 4/1988 | Engelson |
| 4,808,155 A | 2/1989 | Mahurkar |
| 4,819,637 A | 4/1989 | Dormandy, Jr. |
| 4,863,442 A | 9/1989 | DeMello et al. |
| 4,884,579 A | 12/1989 | Engelson |
| 4,927,642 A | 5/1990 | Kunz |
| 4,932,938 A | 6/1990 | Goldberg et al. |
| 4,936,835 A | 6/1990 | Haaga |
| 5,041,090 A | 8/1991 | Scheglov et al. |
| 5,049,140 A | 9/1991 | Brenner et al. |
| 5,080,655 A | 1/1992 | Haaga |
| 5,084,063 A | 1/1992 | Korthoff |
| 5,092,848 A | 3/1992 | deCiutiis |
| 5,108,407 A | 4/1992 | Geremia et al. |
| 5,122,136 A | 6/1992 | Guglielmi et al. |
| 5,192,301 A | 3/1993 | Kamiya et al. |
| 5,207,648 A | 5/1993 | Gross |
| 5,215,530 A | 6/1993 | Hogan |
| 5,221,267 A | 6/1993 | Folden |
| 5,258,042 A | 11/1993 | Mehta |
| 5,263,964 A | 11/1993 | Purdy |
| 5,334,217 A | 8/1994 | Das |
| 5,360,414 A | 11/1994 | Yarger |
| 5,360,418 A | 11/1994 | Weilbacher et al. |
| 5,375,612 A | 12/1994 | Cottenceau et al. |
| 5,395,353 A | 3/1995 | Scribner |
| 5,405,339 A | 4/1995 | Kohnen et al. |
| 5,413,791 A | 5/1995 | Rhee et al. |
| 5,443,454 A | 8/1995 | Tanabe et al. |
| 5,507,731 A | 4/1996 | Hernandez et al. |
| 5,522,883 A | 6/1996 | Slater et al. |
| 5,569,221 A | 10/1996 | Houser et al. |
| 5,570,585 A | 11/1996 | Vaynberg |
| 5,580,568 A | 12/1996 | Greff et al. |
| 5,603,698 A | 2/1997 | Roberts et al. |
| 5,645,558 A | 7/1997 | Horton |
| 5,667,767 A | 9/1997 | Greff et al. |
| 5,683,370 A | 11/1997 | Luther et al. |
| 5,690,644 A | 11/1997 | Yurek et al. |
| 5,695,480 A | 12/1997 | Evans et al. |
| 5,702,361 A | 12/1997 | Evans et al. |
| 5,733,267 A | 3/1998 | Del Toro |
| 5,749,894 A | 5/1998 | Engelson |
| 5,766,219 A | 6/1998 | Horton |
| 5,776,097 A | 7/1998 | Massoud |
| 5,791,036 A | 8/1998 | Goodin et al. |
| 5,795,331 A | 8/1998 | Cragg et al. |
| 5,830,178 A | 11/1998 | Jones et al. |
| 5,833,644 A | 11/1998 | Zando-Azizi et al. |
| 5,895,378 A | 4/1999 | Nita |
| 5,895,385 A | 4/1999 | Guglielmi et al. |
| 5,895,410 A | 4/1999 | Forber et al. |
| 5,902,310 A | 5/1999 | Foerster et al. |
| 5,921,954 A | 7/1999 | Mohr, Jr. et al. |
| 5,928,226 A | 7/1999 | Guglielmi et al. |
| 5,928,260 A | 7/1999 | Chin et al. |
| 5,928,266 A | 7/1999 | Kontos |
| 5,951,599 A | 9/1999 | McCrory |
| 5,957,912 A | 9/1999 | Heitzmann |
| 5,984,964 A | 11/1999 | Roberts et al. |
| 6,010,498 A | 1/2000 | Guglielmi |
| 6,015,424 A | 1/2000 | Rosenbluth et al. |
| 6,022,369 A | 2/2000 | Jacobsen et al. |
| 6,051,607 A | 4/2000 | Greff |
| 6,059,815 A | 5/2000 | Lee et al. |
| 6,063,318 A | 5/2000 | Houser et al. |
| 6,077,260 A | 6/2000 | Wheelock et al. |
| 6,090,125 A | 7/2000 | Horton |
| 6,093,199 A | 7/2000 | Brown et al. |
| 6,102,917 A | 8/2000 | Maitland et al. |
| 6,102,932 A | 8/2000 | Kurz |
| 6,136,015 A | 10/2000 | Kurz et al. |
| 6,146,373 A | 11/2000 | Cragg et al. |
| 6,152,144 A | 11/2000 | Lesh et al. |
| 6,152,913 A | 11/2000 | Feith et al. |
| 6,159,165 A | 12/2000 | Ferrera et al. |
| 6,165,178 A | 12/2000 | Bashiri et al. |
| 6,165,193 A | 12/2000 | Greene, Jr. et al. |
| 6,168,570 B1 | 1/2001 | Ferrera |
| 6,168,615 B1 | 1/2001 | Ken et al. |
| 6,171,326 B1 | 1/2001 | Ferrera et al. |
| 6,179,860 B1 | 1/2001 | Fulton, III et al. |

(56) References Cited

U.S. PATENT DOCUMENTS

| | | |
|---|---|---|
| 6,203,779 B1 | 3/2001 | Ricci et al. |
| 6,224,610 B1 | 5/2001 | Ferrera |
| 6,228,055 B1 | 5/2001 | Foerster et al. |
| 6,238,403 B1 | 5/2001 | Greene, Jr. et al. |
| 6,241,691 B1 | 6/2001 | Ferrera et al. |
| 6,245,053 B1 | 6/2001 | Benjamin |
| 6,258,079 B1 | 7/2001 | Burbank et al. |
| 6,270,477 B1 | 8/2001 | Bagaosian et al. |
| 6,277,126 B1 | 8/2001 | Barry et al. |
| 6,293,960 B1 | 9/2001 | Ken |
| 6,296,622 B1 | 10/2001 | Kurz et al. |
| 6,299,619 B1 | 10/2001 | Greene, Jr. et al. |
| 6,306,124 B1 | 10/2001 | Jones et al. |
| 6,306,153 B1 | 10/2001 | Kurz et al. |
| 6,319,267 B1 | 11/2001 | Kurz |
| 6,322,586 B1 | 11/2001 | Monroe et al. |
| 6,346,091 B1 | 2/2002 | Jacobsen et al. |
| 6,361,528 B1 | 3/2002 | Wilson et al. |
| 6,368,301 B1 | 4/2002 | Hamilton et al. |
| 6,375,774 B1 | 4/2002 | Lunn et al. |
| 6,409,721 B1 | 6/2002 | Wheelock et al. |
| 6,463,317 B1 | 10/2002 | Kucharczyk et al. |
| 6,475,169 B2 | 11/2002 | Ferrera |
| 6,478,773 B1 | 11/2002 | Gandhi et al. |
| 6,494,884 B2 | 12/2002 | Gifford, III et al. |
| 6,497,671 B2 | 12/2002 | Ferrera et al. |
| 6,500,190 B2 | 12/2002 | Greene, Jr. et al. |
| 6,511,468 B1 | 1/2003 | Cragg et al. |
| 6,524,274 B1 | 2/2003 | Rosenthal et al. |
| 6,551,340 B1 | 4/2003 | Konya et al. |
| 6,558,367 B1 | 5/2003 | Cragg et al. |
| 6,585,748 B1 | 7/2003 | Jeffree |
| 6,589,236 B2 | 7/2003 | Wheelock et al. |
| 6,596,217 B1 | 7/2003 | Davis-Lemessy et al. |
| 6,602,261 B2 | 8/2003 | Greene, Jr. et al. |
| 6,607,538 B1 | 8/2003 | Ferrera et al. |
| 6,616,617 B1 | 9/2003 | Ferrera et al. |
| 6,638,291 B1 | 10/2003 | Ferrera et al. |
| 6,656,214 B1 | 12/2003 | Fogarty et al. |
| 6,663,607 B2 | 12/2003 | Slaikeu et al. |
| 6,673,058 B2 | 1/2004 | Snow |
| 6,679,903 B2 | 1/2004 | Kurz |
| 6,689,141 B2 | 2/2004 | Ferrera et al. |
| 6,716,223 B2 | 4/2004 | Leopold et al. |
| 6,723,108 B1 | 4/2004 | Jones et al. |
| 6,730,095 B2 | 5/2004 | Olson, Jr. et al. |
| 6,743,236 B2 | 6/2004 | Barry et al. |
| 6,743,251 B1 | 6/2004 | Eder |
| 6,790,221 B2 | 9/2004 | Monroe et al. |
| 6,835,185 B2 | 12/2004 | Ramzipoor et al. |
| 6,852,261 B2 | 2/2005 | Benjamin |
| 6,905,503 B2 | 6/2005 | Gifford, III et al. |
| 6,966,892 B2 | 11/2005 | Gandhi et al. |
| 6,997,937 B2 | 2/2006 | Jacobsen et al. |
| 7,014,645 B2 | 3/2006 | Greene, Jr. et al. |
| 7,066,904 B2 | 6/2006 | Rosenthal et al. |
| 7,070,608 B2 | 7/2006 | Kurz et al. |
| 7,147,618 B2 | 12/2006 | Kurz |
| 7,179,276 B2 | 2/2007 | Barry et al. |
| 7,182,774 B2 | 2/2007 | Barry et al. |
| 7,198,613 B2 | 4/2007 | Gandhi et al. |
| 7,229,454 B2 | 6/2007 | Tran et al. |
| 7,255,707 B2 | 8/2007 | Ramzipoor et al. |
| 7,316,701 B2 | 1/2008 | Ferrera et al. |
| 7,326,225 B2 | 2/2008 | Ferrera et al. |
| 7,338,511 B2 | 3/2008 | Mirigian et al. |
| 7,507,230 B2 | 3/2009 | Li et al. |
| 7,591,822 B2 | 9/2009 | Olson, Jr. et al. |
| 2001/0001117 A1 | 5/2001 | Chow |
| 2002/0007194 A1 | 1/2002 | Plowiecki |
| 2002/0095174 A1 | 7/2002 | Tsugita et al. |
| 2002/0111646 A1 | 8/2002 | Gifford, III et al. |
| 2002/0165582 A1 | 11/2002 | Porter |
| 2002/0198440 A1 | 12/2002 | Snow |
| 2003/0040733 A1 | 2/2003 | Cragg et al. |
| 2003/0139761 A1 | 7/2003 | Jergensen et al. |
| 2003/0176857 A1 | 9/2003 | Lee |
| 2003/0229277 A1 | 12/2003 | Kolberg et al. |
| 2004/0044330 A1 | 3/2004 | Li et al. |
| 2004/0049153 A1 | 3/2004 | Holman et al. |
| 2004/0133222 A1 | 7/2004 | Tran et al. |
| 2004/0138625 A1 | 7/2004 | Flodin |
| 2004/0186464 A1 | 9/2004 | Mamayek et al. |
| 2004/0225279 A1 | 11/2004 | Raymond |
| 2004/0236364 A1 | 11/2004 | Jones |
| 2004/0254528 A1 | 12/2004 | Adams et al. |
| 2004/0260333 A1 | 12/2004 | Dubrul et al. |
| 2005/0038470 A1 | 2/2005 | van der Burg et al. |
| 2005/0043703 A1 | 2/2005 | Nordgren |
| 2005/0159773 A1 | 7/2005 | Broome et al. |
| 2005/0228360 A1 | 10/2005 | Kelley |
| 2005/0245962 A1 | 11/2005 | Adams et al. |
| 2005/0261725 A1 | 11/2005 | Crawford et al. |
| 2005/0273152 A1* | 12/2005 | Campbell ............... A61F 2/958 623/1.11 |
| 2006/0106421 A1 | 5/2006 | Teoh |
| 2006/0116636 A1 | 6/2006 | Murphy et al. |
| 2006/0142702 A1 | 6/2006 | Sievers et al. |
| 2006/0271085 A1 | 11/2006 | Siess et al. |
| 2007/0178131 A1 | 8/2007 | Yamada et al. |
| 2007/0213764 A1 | 9/2007 | Tran et al. |
| 2008/0045922 A1 | 2/2008 | Cragg et al. |
| 2008/0103476 A1 | 5/2008 | Schulte |
| 2008/0108974 A1 | 5/2008 | Yee Roth |
| 2008/0228173 A1 | 9/2008 | Plowiecki |
| 2008/0294104 A1 | 11/2008 | Mawad |
| 2009/0044811 A1 | 2/2009 | Welchel et al. |
| 2009/0048615 A1 | 2/2009 | McIntosh |
| 2009/1026485 | 10/2009 | Nash et al. |
| 2010/0049165 A1* | 2/2010 | Sutherland ........ A61M 25/0069 604/508 |
| 2012/0157854 A1* | 6/2012 | Kurrus ............... A61M 25/065 600/461 |
| 2014/0135737 A1 | 5/2014 | Sutherland et al. |

FOREIGN PATENT DOCUMENTS

| | | |
|---|---|---|
| DE | 2541919 A1 | 3/1977 |
| DE | 8614013 U1 | 8/1986 |
| DE | 3632573 C1 | 4/1988 |
| DE | 08619671 U1 | 4/1989 |
| DE | 19610333 A1 | 9/1997 |
| DE | 29908453 U1 | 9/1999 |
| DE | 20319306 U1 | 6/2005 |
| EP | 0375775 A1 | 7/1990 |
| EP | 0446804 A2 | 9/1991 |
| EP | 0645161 B1 | 2/2002 |
| EP | 1207791 B1 | 10/2004 |
| FR | 2896421 A1 | 7/2007 |
| JP | 03168156 A | 7/1991 |
| JP | 447416 U | 4/1992 |
| JP | H07503808 | 4/1995 |
| JP | 7508909 A | 10/1995 |
| JP | 11-513606 A | 11/1999 |
| JP | 2001520085 A | 10/2001 |
| JP | 2006509578 A | 3/2006 |
| JP | 2006088079 A | 4/2006 |
| NL | 1008178 C2 | 8/1999 |
| SU | 889009 A1 | 12/1981 |
| WO | 9112847 A1 | 9/1991 |
| WO | 9316505 A1 | 8/1993 |
| WO | 9317745 A1 | 9/1993 |
| WO | 9410936 A1 | 5/1994 |
| WO | 9715257 A | 5/1997 |
| WO | 9715257 A1 | 5/1997 |
| WO | 9727893 A1 | 8/1997 |
| WO | 9920326 A1 | 4/1999 |
| WO | 9922651 A1 | 5/1999 |
| WO | 9939649 A1 | 8/1999 |
| WO | 9942038 A1 | 8/1999 |
| WO | 9948548 A1 | 9/1999 |
| WO | 0001308 A1 | 1/2000 |
| WO | 0115608 A1 | 3/2001 |
| WO | 02096301 A1 | 12/2002 |

(56) References Cited

FOREIGN PATENT DOCUMENTS

| WO | 03013639 | A2 | 2/2003 |
|---|---|---|---|
| WO | 03037419 | A2 | 5/2003 |
| WO | 2004002340 | A1 | 1/2004 |
| WO | 2004054452 | A2 | 7/2004 |
| WO | 2004062511 | A1 | 7/2004 |
| WO | 2007039678 | A1 | 4/2007 |

OTHER PUBLICATIONS

Notice of Final Rejection, and translation thereof, from counterpart Korean Patent Application No. 10-2013-69432, dated Feb. 26, 2015, 7 pp.

Notification of the First Office Action, and translation thereof, from counterpart Chinese Patent Application No. 201310240253.1, dated Dec. 9, 2014, 17 pp.

Notice of Preliminary Rejection, and translation thereof, from counterpart Korean Patent Application No. 10201369432, dated Aug. 29, 2014, 10 pp.

Notice of Reasons for Rejection, and translation thereof, from counterpart Japanese Patent Application No. 2013119620, dated Apr. 30, 2014, 16 pp.

Office Action from counterpart Canadian Patent Application No. 2815040, dated Jun. 4, 2014, 3 pp.

Office Action from counterpart Canadian Application No. 2,815,040, dated May 19, 2015, 3 pp.

Balt Extrusion, Sonic Flow-Directed Braided Microcatheter, www.balt.fr, 2008, 4 pp.

Byrne, "Review Article: Endovascular Treatments for Intracranial Aneurysms," The British Journal of Radiology, vol. 69, No. 826, Oct. 1996, pp. 891-899.

Jeffree et al., "The Porous, Guidewire-Directed, Detachable Aneurysm Liner: A New Concept in the Endovascular Treatment of Intracranial Aneurysms," American Journal of Neuroradiology, vol. 20, May 1999, pp. 774-779.

Kassell et al., "Size of Intracranial Aneurysms," Neurosurgery, vol. 12, No. 3, Mar. 1983, pp. 291-297.

Schievink, "Intracranial Aneurysms," The New England Journal of Medicine, vol. 336, No. 1, Jan. 2, 1997, pp. 28-40.

Szikora et al., "Combined Use of Stents and Coils to Treat Experimental Wide-Necked Carotid Aneurysms: Preliminary Results," American Journal of Neuroradiology, vol. 15, Jun. 1994, pp. 1091-1102.

Szikora et al., "Endovascular Treatment of Experimental Aneurysms with Liquid Polymer: The Protective Potential of Stents," Neurosurgery, vol. 38, No. 2, Feb. 1996, pp. 339-347.

Turjman et al., "Combined Stent Implantation and Endosaccular Coil Placement for Treatment of Experimental Wide-Necked Aneurysms: A Feasibility Study in Swine," American Journal of Neuroradiology, vol. 15, Jun. 1994, pp. 1087-1090.

Yoshimoto et al., "Cerebral Aneurysms Unrelated to Arterial Bifurcations," Acta Neurochirurgica, The European Journal of Neurosurgery, vol. 138, No. 8, 1996, pp. 958-964.

Notice of Last Preliminary Rejection, and translation thereof, from counterpart Korean Patent Application No. 10-2013-0069432, dated Jun. 26, 2015, 9 pp.

Second Office Action, and translation thereof, from counterpart Chinese Patent Application No. 201310240253.1, dated Sep. 1, 2015, 14 pp.

Second Final Rejection, and translation thereof, from counterpart Korean Application No. 10-2013-0069432, dated Aug. 5, 2016, 5 pp.

Notice of Preliminary Rejection, and translation thereof, from counterpart Korean Application No. 10-2013-0069432, dated Dec. 30, 2015, 9 pp.

Office Action, and English translation thereof, from counterpart Indian Application No. 1409/DEL/2013, dated Aug. 17, 2018, 6 pp.

* cited by examiner

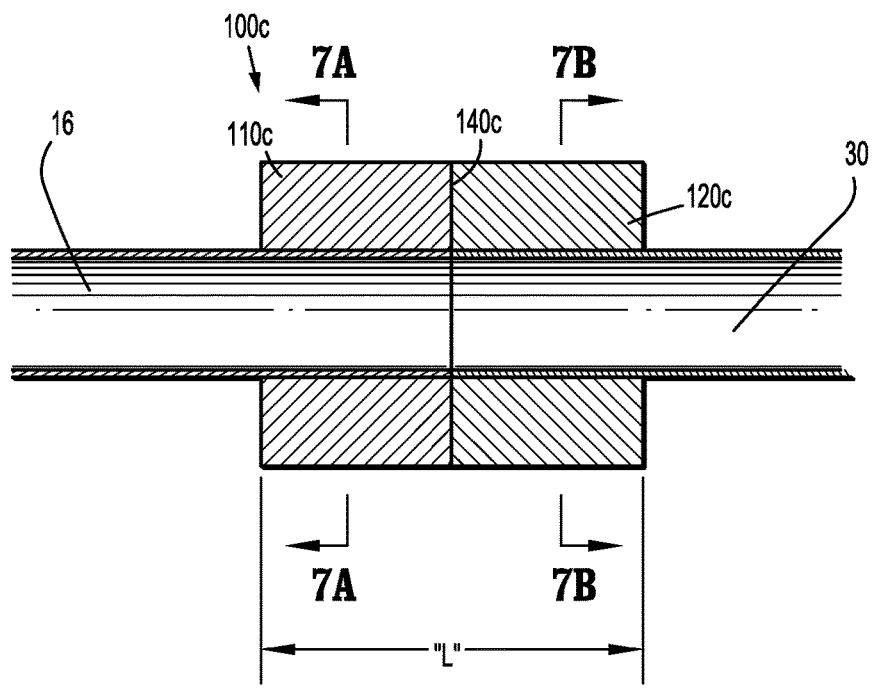
FIG. 7
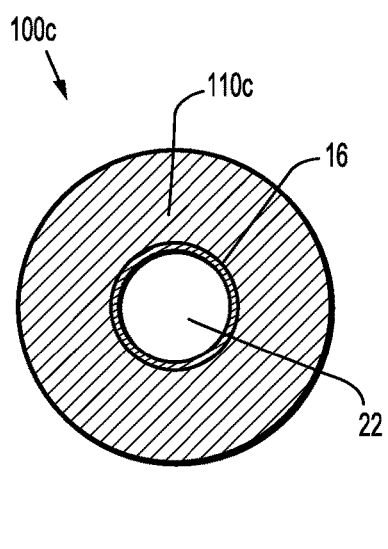 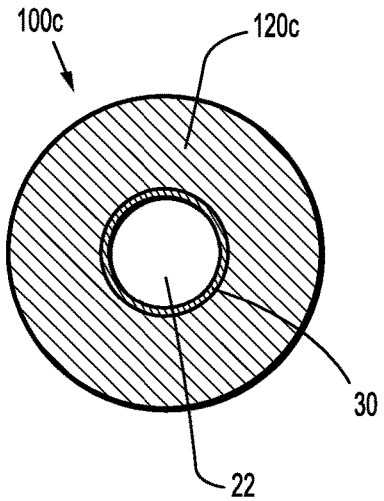
FIG. 7A          FIG. 7B

DETACHABLE COUPLING FOR CATHETER

BACKGROUND

1. Technical Field

The present disclosure generally relates to microcatheters, and, in particular, a microcatheter with a detachable, biocompatible tip.

2. Description of Related Art

Microcatheters are generally inserted into the body through a blood vessel such as the femoral artery and have a variety of uses in the vasculature. Microcatheters may be used to assist in the treatment of various neurovascular conditions such as arteriovenous malformations (AVMs) and aneurysms.

Aneurysms and AVMs may be treated intravascularly with compositions delivered through microcatheters which solidify in vivo so as to permanently occlude blood flow to cerebral aneurysms and cerebral arteriovenous malformations. Suitable intravascular compositions include, by way of example only, cyanoacrylates which polymerize in vivo to form a solid mass as well as solutions of a biocompatible, water insoluble polymer dissolved in a non-aqueous solvent such as dimethyl sulfoxide ("DMSO") whereupon introduction into the vasculature, the DMSO dissipates and the polymer precipitates in the aqueous based blood composition. Such intravascular compositions further comprise a contrast agent to assist in visualization of the formed mass.

Embolic compositions are delivered to the embolization site from a microcatheter. As the embolic composition solidifies in vivo there may be "flow back" or "reflux" of the composition such that the distal tip of the microcatheter becomes entrapped there within. When this occurs, the clinician either must attempt to withdraw the microcatheter by force, often resulting in microcatheter breakage, or must cut the catheter, leaving the distal tip within the patient's vasculature.

SUMMARY

Accordingly, the present disclosure is directed to providing a microcatheter which can be safely removed from the patient in the event the distal tip becomes trapped in the vasculature for any reason, while minimizing the potential risks caused by such complications.

The present disclosure is directed to a microcatheter comprising an elongate flexible tubular body, a tip body and a coupling. The elongate flexible tubular body has a proximal end, a distal end and at least one lumen extending axially therethrough. The tip body has a proximal end and a distal end and a lumen extending axially therethrough. The coupling covers a portion of both the tubular body and tip body and is made from a first material and a second material, where the first material is different from the second material. The first material is compatible with an outermost layer of the tubular body and an outermost layer of the tip body. The second material is configured to form a detachable bond with at least one of the tubular body and the tip body.

In disclosed embodiments, the first material is disposed radially outwardly of the second material, e.g., along an entire length of the second material. Here, it is disclosed that the first material is disposed radially outwardly of the second material along an entire length of the first material.

In disclosed embodiments, the second material is in direct contact with the tubular body.

In disclosed embodiments, the first material is selected from the group consisting of Polyurethane, Polyethylene, Polytetrafluoroethylene (PTFE), Expanded Polytetrafluoroethylene (EPTFE), Polyether block amide, Polyvinyl chloride (PVC), and Polypropylene. In disclosed embodiments, the second material is selected from the group consisting of Low Density Polyethylene (LDPE), Linear Low Density Polyethylene (LLDPE) and High-density polyethylene (HDPE). Here, it is disclosed that the tubular body is made from the first material.

In disclosed embodiments, a third material is disposed between the first material and the second material.

In disclosed embodiments, the first material is compatible with a hydrophilic coating.

In disclosed embodiments, the coupling is a single unit.

In disclosed embodiments, a hydrophilic coating is included and is in contact with the tubular body, the tip body and the first material.

In disclosed embodiments, a hydrophilic coating is in contact with the tubular body, the tip body and the first material.

The present disclosure is also directed to a microcatheter comprising a tubular body, a tip body and a coupling. The tubular body has a proximal portion, a distal portion, and a lumen extending from the proximal portion to the distal portion for introducing a fluid agent. The tubular body is made from a first material. The tip body is coupled to the distal portion of the tubular body and defines a central lumen communicating with the lumen of the tubular. The coupling is engaged with a portion of the tubular body via a first bond, and engaged with a portion of the tip body via a second bond. The coupling is made from at least two different materials including the first material and a second material. The first bond and the second bond have different bond strengths.

In disclosed embodiments, the first bond is stronger than the second bond.

In disclosed embodiments, the first material is selected from the group consisting of Polyurethane, Polyethylene, Polytetrafluoroethylene (PTFE), Expanded Polytetrafluoroethylene (EPTFE), Polyether block amide, Polyvinyl chloride (PVC), and Polypropylene. In disclosed embodiments, the second material is selected from the group consisting of Low Density Polyethylene (LDPE), Linear Low Density Polyethylene (LLDPE) and High-density polyethylene (HDPE).

The present disclosure is also directed to a method of manufacturing a microcatheter. The method comprises providing an elongate flexible tubular body having a proximal end, a distal end and at least one lumen extending axially therethrough. The method also comprises providing a tip body having a proximal end and a distal end and a lumen extending axially therethrough. The method further comprises providing a coupling made of a first material and a second material, where the first material is different from the second material, and where the first material is compatible with an outermost layer of the tubular body and an outermost layer of the tip body. The method also comprises heating a portion of the tubular body and a portion of the coupling to form a first bond therebetween, heating a portion of the tip body and a portion of the coupling to form a second bond therebetween. The first and second bonds have different bond strengths.

BRIEF DESCRIPTION OF THE DRAWINGS

Embodiments of the present disclosure will be readily appreciated by reference to the drawings wherein:

FIG. 7 is a longitudinal cross-sectional view of a third embodiment of a coupling in accordance with the present disclosure;

FIG. 7A is a transverse cross-sectional view of the coupling of FIG. 7 taken along line 7A-7A; and FIG. 7B is a transverse cross-sectional view of the coupling of FIG. 7 taken along line 7B-7B.

DESCRIPTION

In the following description, the terms "proximal" and "distal" as used herein refer to the relative position of the microcatheter in a lumen. The "proximal" or "trailing" end of the microcatheter is the microcatheter segment extending outside the body closest to the clinician. The "distal" or "leading" end of the microcatheter is the microcatheter segment placed farthest into a body lumen from the entrance site.

Figure 1:
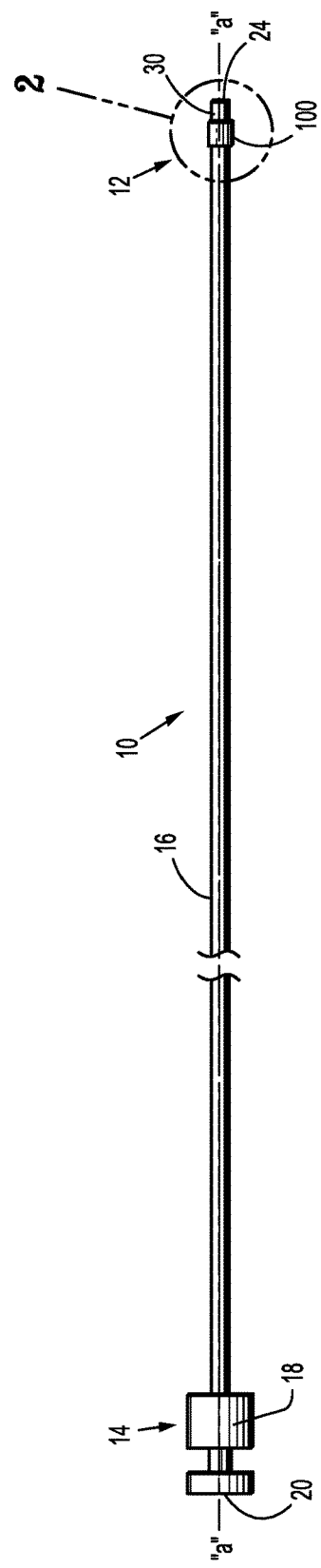
FIG. 1 is a side plan view of a catheter in accordance with the present disclosure.

With reference to FIG. 1, a microcatheter 10 can be useful for delivering embolic agents to vascular sites of patients. Though microcatheters can be used in any vessel in the body, they are particularly useful for embolizing aneurysms or AVMs in the neurovasculature. Microcatheter 10 includes a tubular body segment 16 defining longitudinal axis "a" and having a distal or leading end 12 and a proximal or trailing end 14. Microcatheter 10 further includes a tip body 30 which is coaxial with the tubular body 16 and detachably connected or engaged to tubular body 16 through a coupling 100. The term "detachably engaged" or "detachably connected" is intended to include an interpretation where tip body 30 may be released from tubular body 16 upon application of a retraction force that may be a predetermined value depending on the intended use of the microcatheter 10. For example, the predetermined force may be a tensile force applied along the longitudinal axis "a" to at least one of tubular body 16, tip body 30 or coupling 100. In other embodiments, the predetermined force may be a shearing or radial force applied to the components. The term "retraction force" is generally a tensile force applied along the longitudinal axis of the microcatheter 10, for example, parallel to a central lumen 22, in the proximal direction, that is in the direction that would withdraw the microcatheter from the patient. The retraction force used to detach the tubular body 16 from the tip body 30 can, for example, be no more than about 160 gram-force and more particularly can range from about 10 gram-force to about 160 gram-force. In certain embodiments, the retraction force is about 20 gram-force to about 40 gram-force. In other embodiments, the retraction force is about 30 gram-force to about 50 gram-force. Other ranges than those described above can also be used. Various embodiments of coupling 100 will be discussed in greater detail hereinbelow.

Figure 2:
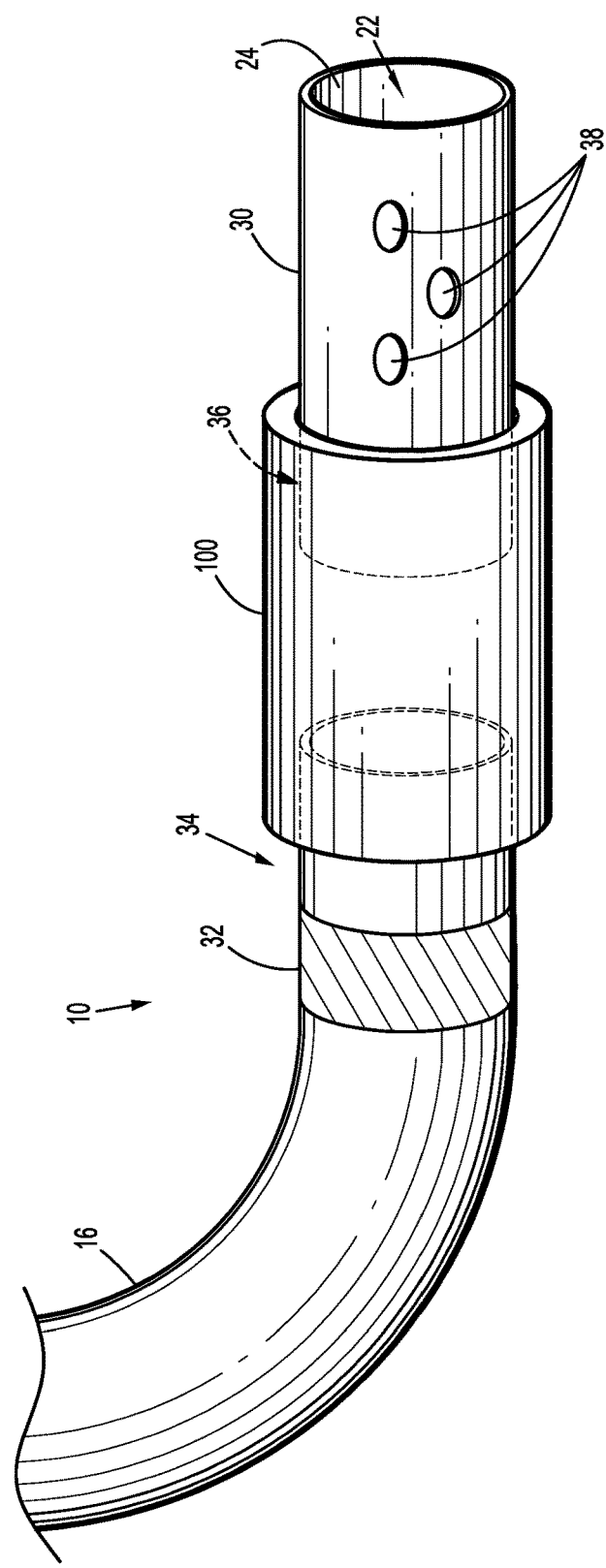
FIG. 2 is a perspective view of a portion of the catheter of FIG. 1 illustrating the tubular body, tip body and coupling.

Referring to FIGS. 1 and 2, the tubular body 16 and the tip body 30 can be of the same or different outer and inner diameters. The proximal end 14 of microcatheter 10 may include a manifold 18. Manifold 18 may include at least one access port 20 in fluid communication with a distal access port 24 by way of an elongate central lumen 22. Central lumen 22 permits the microcatheter 10 to track over a guidewire (not shown). After removal of the guidewire, the central lumen 22 may be used to deliver an embolic agent to the desired vascular site. Although not specifically illustrated, the microcatheter 10 may contain a plurality of lumens. For example, one lumen may be dedicated for use by a guidewire, while another lumen may be dedicated to delivery of the embolic agent. The microcatheter 10 may include a marker 32, for example a radiopaque marker, located adjacent the distal end 12 of the tubular body 16. The marker 32 can be a ring or band made from a metal or metal alloy, such as platinum, platinum/iridium, gold, nitinol and the like. In disclosed embodiments, coupling 100 may be filled with a radiopaque material, such as barium sulfate.

To further assist in the delivery of the embolic agent to the desired vascular site, the tip body 30 may optionally contain a plurality of lateral apertures or holes 38. The shape of the apertures 38 may be selected from round, elliptical, or other shapes.

The total length of the microcatheter 10 can generally be in the range of from about 150 cm to about 175 cm, although other ranges are also possible. The tubular body 16 can be selected to have an outside diameter within the range of about 0.5 mm to about 1.5 mm, although other diameters are also possible. In some embodiments, the diameter of the central lumen 22 can be between about 0.002 inches and about 0.005 inches larger than the outside diameter of the guidewire, if one is used. This diameter can be modified appropriately at the proximal and distal ends. Other dimensions than those described herein can be readily utilized by those of ordinary skill in the art in view of the disclosure herein to suit particular intended uses of the microcatheter 10.

The tubular body 16 can be constructed of a variety of materials and in a variety of ways. It is envisioned that the tubular body 16 is made from a material selected from the group consisting of Polyurethane, Polyethylene, Polytetrafluoroethylene (PTFE), Expanded Polytetrafluoroethylene (EPTFE), Polyether block amide (including those branded Pebax®), Polyvinyl chloride (PVC), and Polypropylene. In disclosed embodiments, the tubular body 16 may be constructed of a material that is compatible with dimethylsulfoxide. The tubular body 16 may also contain zones with varying flexibility which can also be controlled by the methods of construction and materials employed. The tubular body 16 may also be constructed by layering various polymers, such polyimide, polytetrafluoroethylene, polyether block amides, polyamide and the like. The tubular body 16 may additionally include a braid of varying pitches. The tip body 30 is made from a biocompatible material. What is meant by "biocompatible" is that the material, in the amounts employed, are substantially non-toxic and substantially non-immunogenic when used in the vasculature of a patient. For example, it is envisioned that the tip body 30 is made from a material selected from the group consisting of Polyurethane, Polyethylene, Polytetrafluoroethylene (PTFE), Expanded Polytetrafluoroethylene (EPTFE), Polyether block amide, Polyvinyl chloride (PVC), and Polypropylene. It is further envisioned that the tip body 30 is made from the same material as the tubular body 16.

In certain embodiments, the tip body 30 can also be "biodegradable." A wide variety of biodegradable/bioerodable and non-biodegradable materials are known which are useful for constructing microcatheter tips. The tip body 30 can be formed of a material which is biodegradable or bioabsorbable in situ. Biodegradable or bioabsorbable materials, or some combination thereof, can be used which allow for the biodegradation/bioabsorption in predetermined conditions.

A variety of biocompatible-biodegradable materials are commercially available and suitable for use in these embodiments. Examples of these materials include DLPLA-poly (dl-lactide), LPLA-poly(1-lactide), PGA-polyglycolide, PDO-poly(dioxanone), PGA-TMC-poly(glycolide-co-trimethylene carbonate), PGA-LPLA-poly(1-lactide-co-glycolide), PGA-DLPLA-poly(dl-lactide-co-glycolide), LPLA-DLPLA-poly(1-lactide-co-dl-lactide), and PDO-PGA-TMC-poly(glycolide-co-trimethylene carbonate-co-dioxanone).

It is further envisioned that a lubricious coating may be disposed over components of microcatheter 10, including tubular body 16, coupling 100 and tip body 30. Suitable lubricious coatings include hydrophilic materials such as polyvinylpyrrolidone (PVP), polyethylene oxide, polyethylene glycol, cellulosic polymers, and hydrophilic maleic anhydride, or hydrophobic materials such as silicone, PTFE, or FEP. These coatings are typically applied by dip coating or spray methods, and heat or Ultraviolet (UV) curing may be used. For example, cure temperatures up to about 70 degrees C. are used for silicone coatings, and several hundred degrees C. may be required for PTFE coatings. In addition to the lubricious coating, bioactive coatings may be applied over all or part of the microcatheter. Such coatings also may incorporate materials such as heparin, hirudin and its analogs, or other chugs. These coatings typically are applied by dip coating. Bioactive coatings are desirable to prevent blood clotting or for delivery of drugs to a specific site.

Figure 5:
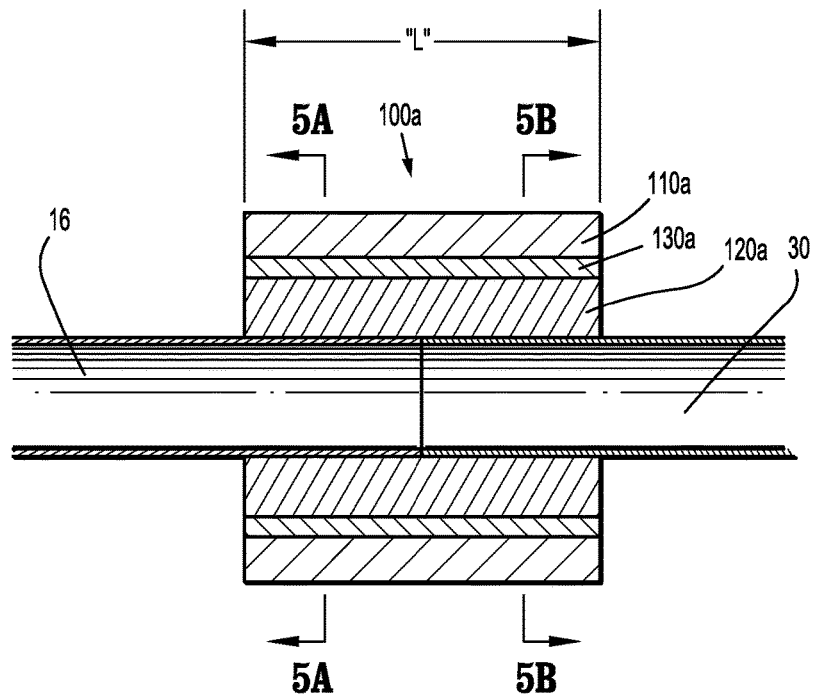
FIG. 5 is a longitudinal cross-sectional view of a first embodiment of a coupling in accordance with the present disclosure.
Figure 5A:
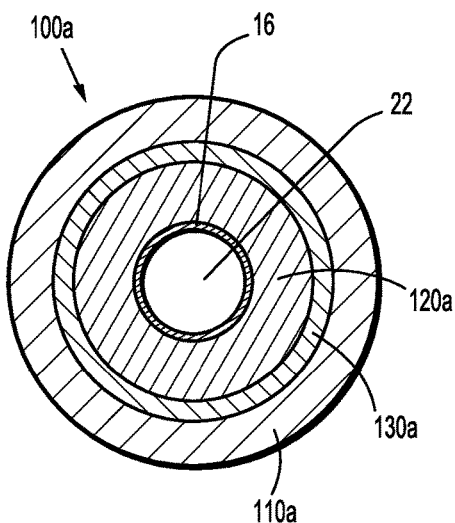
FIG. 5A is a transverse cross-sectional view of the coupling of FIG. 5 taken along line 5A-5A.
Figure 5B:
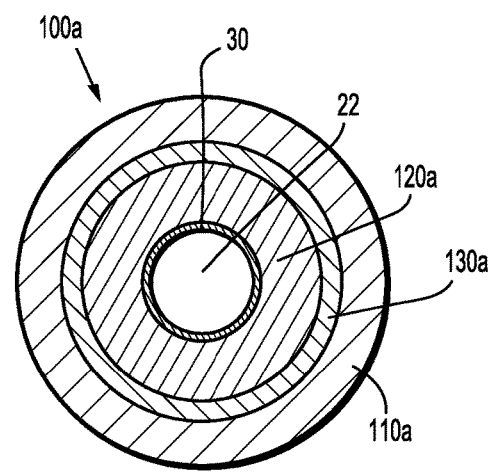
FIG. 5B is a transverse cross-sectional view of the coupling of FIG. 5 taken along line 5B-5B.

Various embodiments of coupling 100 are shown in the accompanying figures. With reference to FIGS. 5-5B, a first embodiment of a coupling 100a is shown. Coupling 100a is made from a first material 110a, and a second material 120a. Additionally, an optional third material 130a is shown between first material 110a and second material 120a and may be used to form a bond therebetween. In the embodiment illustrated in FIGS. 5-5B, first material 110a, and second material 120a extend the entire length "L" of coupling 100a. Additionally, first material 110a is disposed radially outwardly of second material 120a along the entire length "L" of coupling 100a.

It is envisioned that first material 110a of coupling 100a includes a material that is compatible with an outermost layer of the tubular body 16 and the outermost layer of the tip body 30, such as a hydrophilic coating, as discussed above. As can be appreciated, materials that are compatible with a hydrophilic coating include materials that the hydrophilic coating can adhere to by dipping, sponge coating, spraying, or any other conventional coating techniques well known in the art. For example, it is envisioned that first material 110a includes Polyurethane, Polyethylene, Polytetrafluoroethylene (PTFE), Expanded Polytetrafluoroethylene (EPTFE), Polyether block amide, Polyvinyl chloride (PVC), or Polypropylene. It is further envisioned that first material 100a is the same material that tubular body 16 is made from.

With regard to second material 120a of coupling 100a, it is envisioned that second material 120a includes a material that is capable of forming a bond with tubular body 16 and a detachable bond with tip body 30. Accordingly, it is envisioned that second material 120a of coupling 100a includes Low Density Polyethylene (LDPE), Linear Low Density Polyethylene (LLDPE) or High-density polyethylene (HDPE), for example. In embodiments where tubular body 16 is made from the same material as tip body 30, for example, it is envisioned that forming the bonds with different bond strengths is accomplished by heating the bonds at different temperatures. For example, to provide a relatively strong bond between tubular body 16 and coupling 100a, the bond could be created by heating the area at a temperature of between about 350° F. and about 354° F., for example, and for a duration of about 7 seconds, for example; to provide a relatively weak bond between tip body 30 and coupling 100a, the bond could be created by heat the area at a temperature of between about 246° F. and about 250° F., for example, and for a duration of about 6 seconds, for example.

Thus, in disclosed embodiments, the coupling 100a is attached to tubular body 16 via a strong bond relative to the strength of the bond connecting coupling 100a and tip body 30. In these embodiments, a suitable retraction force applied by a clinician would result in coupling 100a detaching from tip body 30, and coupling 100a remaining connected to tubular body 16. As can be appreciated, the strong bond and weak bond can be switched depending on the desired results. In a disclosed embodiment, first material 110a is a Polyether block amide, second material 120a is a Low Density Polyethylene, and at least a portion of tubular body 16 is a Polyether block amide.

Additionally, third material 130a, which may be used to form a bond between first material 110a and second material 120a, can be made from Plexar, TYMAX™, or Dupont™ Bynel®. In particular, it is envisioned that when first material 110a is made from Pebax, and when second material 120a is made from LDPE, third material 130a is made from Plexar.

Figure 6:
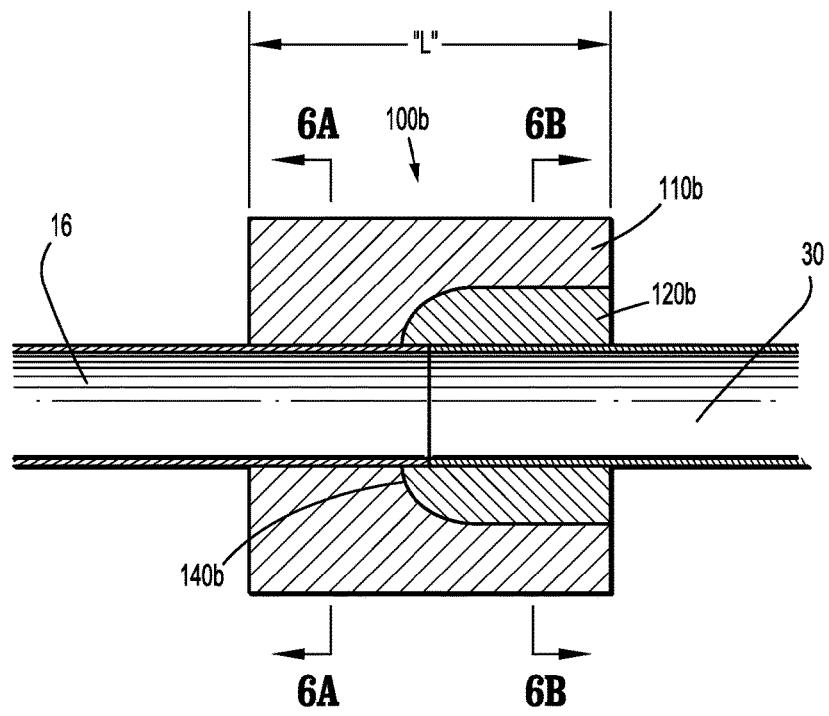
FIG. 6 is a longitudinal cross-sectional view of a second embodiment of a coupling in accordance with the present disclosure.
Figure 6A:
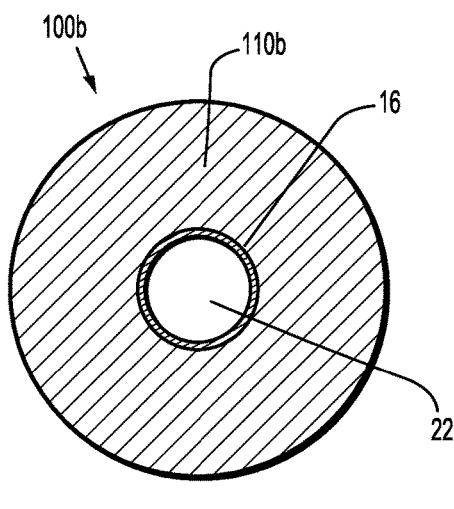
FIG. 6A is a transverse cross-sectional view of the coupling of FIG. 6 taken along line 6A-6A.
Figure 6B:
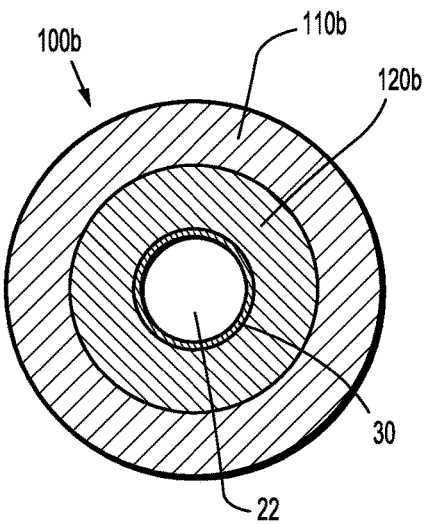
FIG. 6B is a transverse cross-sectional view of the coupling of FIG. 6 taken along line 6B-6B.

With reference to FIGS. 6-6C, a second embodiment of coupling 100 is shown and is indicated as coupling 100b. Coupling 100b is made from a first material 110b and a second material 120b. As shown, first material 110b is disposed radially outwardly of second material 120b along the entire length of second material 120b. Additionally, there is a line of distinction 140b between first material 110b and second material 120b, such that second material 120b only extends a portion of the length "L" of coupling 100b. While the line of distinction 140b is shown near the longitudinal midpoint of coupling 100b, it is envisioned that the line of distinction 140b is located farther proximally or distally than the location shown. Additionally, it is envisioned that first material 110b is selected from the same group of materials as first material 110a, and second material 120b is selected from the same group of materials as second material 120a. Further, while not explicitly illustrated, a third material may be disposed between first material 110b and second material 120b, and may include the same material(s) as third material 130a.

With reference to FIGS. 7-7C, a third embodiment of coupling 100 is shown and is indicated as coupling 100c. Coupling 100c is made from a first material 110c and a second material 120c. As shown, the entirety of first material 110c is disposed proximally of the entirety second material 120c. Additionally, there is a line of distinction 140c between first material 110c and second material 120c. While the line of distinction 140c is shown near the longitudinal midpoint of coupling 100c and adjacent the junction of tubular body 16 and tip body 30, it is envisioned that the line of distinction 140c is located farther proximally or distally than the location shown. Additionally, it is envisioned that first material 110c is selected from the same group of materials as first material 110a, and second material 120c is selected from the same group of materials as second material 120a. Further, while not explicitly illustrated, a third material may be disposed between first material 110c and second material 120c, and may be selected from the same group of materials as third material 130a.

Referring back to FIG. 3, the use of the microcatheter 10 within the human body is illustrated. Specifically, the microcatheter 10 is inserted into the patient in a convenient location, such as the groin. The microcatheter 10 is advanced through the vasculature until the tip body 30 reaches a treatment site 40, such as for example an AVM or aneurysm. The position of the microcatheter 10 can be monitored by visualizing the radiopaque marker 32. Once the microcatheter 10 is in its appropriate position in the vasculature, embolic agent 42 can be delivered to the treatment site 40. The embolic agent 42 can be a liquid embolic agent and can comprise of a number of materials. Suitable embolic agents 42 include those containing biocompatible polymers and prepolymers which polymerize in situ. The liquid embolic agent can also comprise a biocompatible solvent and a contrast agent. In one embodiment, the contrast agent is water-insoluble. One such example is Onyx™, a non-adhesive liquid embolic agent comprised of EVOH (ethylene vinyl alcohol) copolymer dissolved in DMSO (dimethyl sulfoxide) and suspended micronized tantalum powder to provide contrast for visualization under fluoroscopy, commercially available from Tyco Healthcare Group LP dba Covidien, Irvine, Calif. Further description of suitable embolic agents are described in U.S. Pat. Nos. 5,667,767; 5,695,480; 6,051,607; 6,342,202; 6,531,111; and 6,562,317 all of which are incorporated by reference herein and made a part of this specification.

Figure 3:
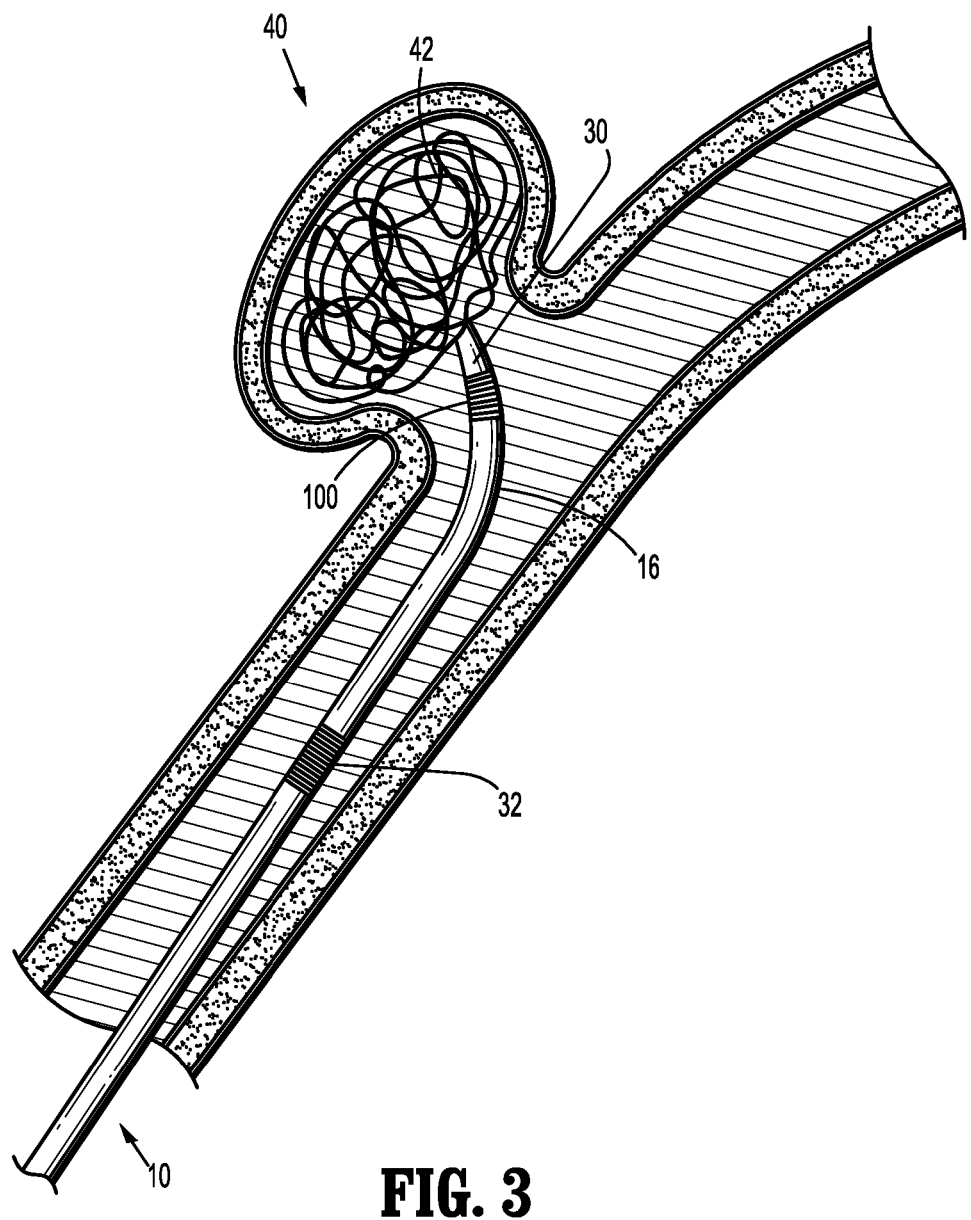
FIGS. 3 and 4 illustrate the catheter of FIGS. 1 and 2 in use within a tortuous region of the vasculature of a patient in accordance with the principles of the present disclosure.
Figure 4:
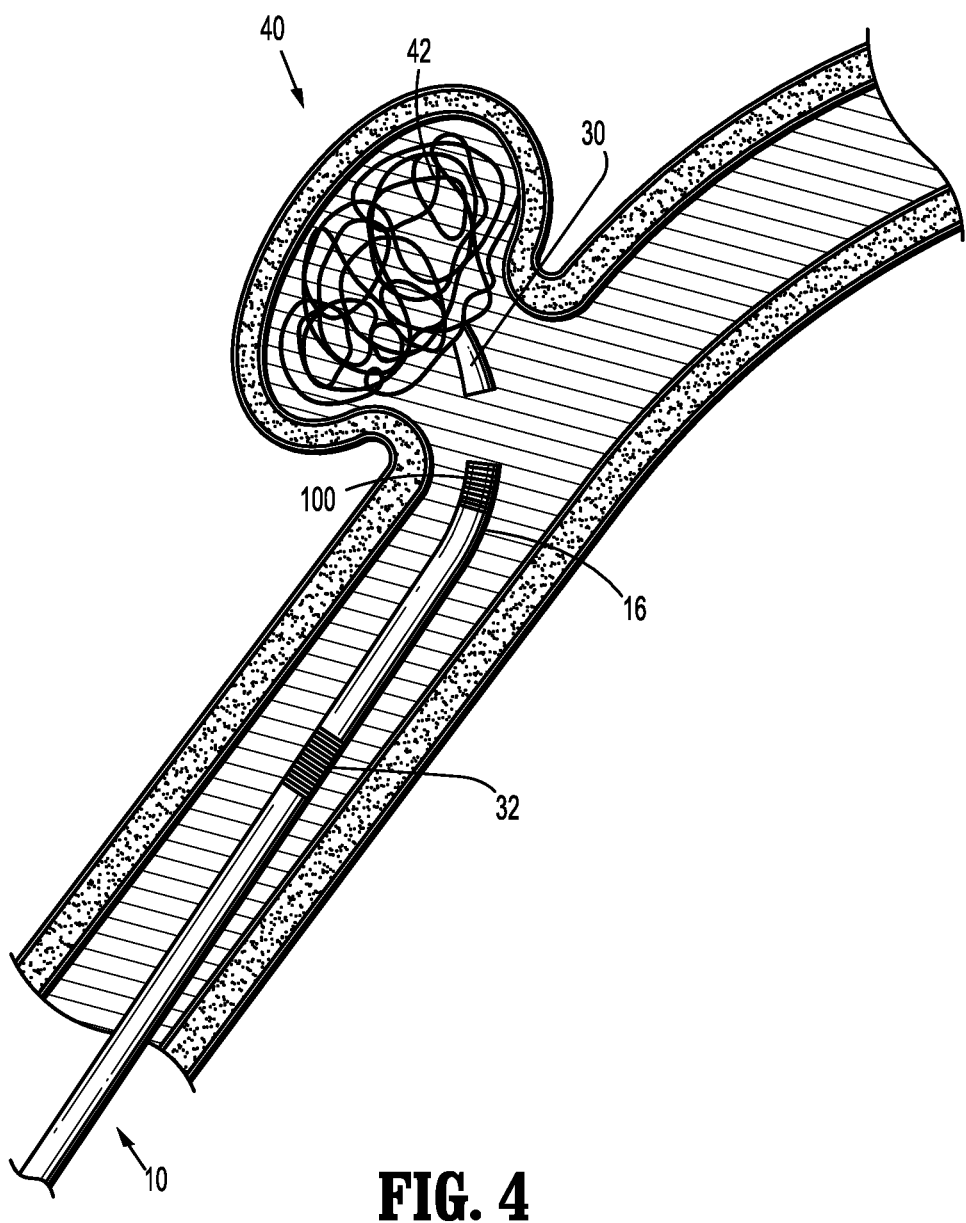

Referring to FIGS. 3 and 4, after delivery of the embolic agent 42, the tip body 30 can be entrapped within the agent 42. To remove the microcatheter 10 from the patient, the attending clinician can apply a retraction force to the tubular body 16. Generally, when the retraction force is applied, the coupling 100 can either 1) remain attached to the tip body 30; 2) remain attached to the tubular body 16; or 3) break into two components thereby remaining partially attached to both the tubular body 16 and the tip body 30.

The condition of the coupling 100 after application of the force can be influenced by the materials of construction of the components and the approach utilized in engaging the coupling 100 to the tip body 30 and the tubular body 16. The engagement of the tip body 30 to the coupling 100 and the engagement of the tubular body 16 to the coupling 100 can be accomplished in variety of ways. For example, the coupling 100 can overlap with a distal end 34 of the tubular body 16 and/or can overlap with a proximal end 36 of the tip body 30 (see FIG. 2). The amount of overlap can be a factor in determining the retraction force used for detaching the tip body 30. In some embodiments, one or both attachments of the coupling 100 to the tip body 30 or the tubular body 16 can be a butt joint (end to end). In some embodiments, the distal end 34 and proximal end 36 can form a butt joint.

The present disclosure also relates to a method of manufacturing microcatheter 10 and/or coupling 100, as disclosed herein. Accordingly, it is envisioned that coupling 100 for use with microcatheter 10 is made via coextrusion or from a mold (e.g., molding or overmolding). Additionally, as discussed above, it is envisioned that coupling 100 is bonded to catheter 10 via hot bonding. It particular, coupling 100 may be bonded to tubular body 16 by heating coupling 100/tip body 16 to a temperature of between about 350° F. and about 354° F. for about 7 seconds, and coupling 100 may be bonded to tip body 30 by heating coupling 100/tip body 30 to a temperature of between about 246° F. and about 250° F. for about 6 seconds. When the heat source is applied, the coupling 100 can attach to the tubular body 16 and the tip body 30 by either a mechanical bond (force of the heat shrinking around the smaller tubular body 16 and tip body 30) or a fused bond (where the materials of the coupling 100, the tubular body 16, and/or the tip body 30 are melted together).

In an alternative method of construction, the coupling 100 can be attached to the tip body 30 and/or tubular body 16 by use of adhesives, hot air, laser, hot die, plasma treating or solvent bonding.

It is further envisioned that there can be varying amounts of overlap of the coupling 100 with the tubular body 16 and/or the tip body 30. The amount of overlap can be one factor in the retraction force required to separate the tip body 30 from the tubular body 16 and/or coupling 100. For example, it is envisioned that the larger the overlap of the coupling 100 on either the tubular body 16 and/or the tip body 30, the greater the retraction force required to detach the two components. In some embodiments, this overlap can be from about 0.5 mm to about 5 mm. In some embodiments, the overlap can be between about 2 mm to about 4 mm. Other overlap ranges are also possible.

The above description and the drawings are provided for the purpose of describing embodiments of the present disclosure and are not intended to limit the scope of the disclosure in any way. For example, while each embodiment of coupling 100a-100c illustrates tubular body 16 in contact with tip body 30, it is envisioned that there is a space therebetween. It will be apparent to those skilled in the art that various modifications and variations can be made without departing from the spirit or scope of the disclosure. Thus, it is intended that the present disclosure cover the modifications and variations of this disclosure provided they come within the scope of the appended claims and their equivalents.

What is claimed is:
1. A microcatheter comprising:
an elongate flexible tubular body having a proximal end, a distal end and at least one lumen extending axially therethrough;
a tip body having a proximal end and a distal end and a lumen extending axially therethrough;
a coupling covering a portion of both the tubular body and tip body, the coupling comprising a first layer and a second layer made from different materials, the first layer being made from a first material and the second layer being made from a second material, wherein the first material is different from the second material; and
a hydrophilic coating applied to at least the coupling and the tip body,
wherein the first material of the coupling is compatible with the hydrophilic coating, and wherein the second material of the coupling is configured to form a detachable bond with at least one of the tubular body and the tip body.

2. The microcatheter of claim 1 wherein the first layer is disposed radially outwardly of the second layer.

3. The microcatheter of claim 2 wherein the first layer is disposed radially outwardly of the second layer along an entire length of the second layer.

4. The microcatheter of claim 3 wherein the first layer is disposed radially outwardly of the second layer along an entire length of the coupling.

5. The microcatheter of claim 1 wherein the second layer is in direct contact with the tubular body.

6. The microcatheter of claim 5 wherein the second layer of the coupling is in direct contact with the tubular body and with the tip body.

7. The microcatheter of claim 1 wherein the first material is selected from the group consisting of Polyurethane, Polyethylene, Polytetrafluoroethylene (PTFE), Expanded Polytetrafluoroethylene (EPTFE), Polyether block amide, Polyvinyl chloride (PVC), and Polypropylene.

8. The microcatheter of claim 7 wherein the tubular body is made from the first material.

9. The microcatheter of claim 1 wherein the second material is selected from the group consisting of Low Density Polyethylene (LDPE), Linear Low Density Polyethylene (LLDPE) and High-density polyethylene (HDPE).

10. The microcatheter of claim 1 wherein the tubular body is made from the first material.

11. The microcatheter of claim 1 wherein the first material is Polyether block amide and wherein the second material is Low Density Polyethylene, and wherein at least a portion of the tubular body is made from Polyether block amide.

12. The microcatheter of claim 1 further comprising a third layer made from a third material, the third layer being disposed between the first layer and the second layer.

13. The microcatheter of claim 1 wherein the coupling is a single unit.

14. The microcatheter of claim 1 wherein the hydrophilic coating is in contact with the tubular body, the tip body and the first layer of the coupling.

15. The microcatheter of claim 1 wherein the first layer does not contact the tip body.

16. The microcatheter of claim 1 wherein the first layer extends along an entire length of the coupling.

17. The microcatheter of claim 1 wherein the first and second layers each only extends along a portion of a length of the coupling.

18. The microcatheter of claim 1 wherein the coupling is configured such that an entirety of the first material is disposed proximally of an entirety of the second material.

19. A microcatheter comprising:
a tubular body having a proximal portion, a distal portion, and a lumen extending from the proximal portion to the distal portion for introducing a fluid agent, the tubular body being made from a first material;
a tip body coupled to the distal portion of the tubular body and defining a central lumen communicating with the lumen of the tubular body;
a coupling engaged with a portion of the tubular body via a first bond, and engaged with a portion of the tip body via a second bond, the coupling comprising a first layer and a second layer being made from different materials, the first layer being made from the first material and the second layer being made from a second material, wherein the first bond and the second bond have different bond strengths; and
a hydrophilic coating applied to at least the coupling and the tip body, the first material of the coupling being compatible with the hydrophilic coating.

20. The microcatheter of claim 19 wherein the first bond is stronger than the second bond.

21. The microcatheter of claim 19 wherein the first material is selected from the group consisting of Polyurethane, Polyethylene, Polytetrafluoroethylene (PTFE), Expanded Polytetrafluoroethylene (EPTFE), Polyether block amide, Polyvinyl chloride (PVC), and Polypropylene.

22. The microcatheter of claim 21 wherein the second material is selected from the group consisting of Low Density Polyethylene (LDPE), Linear Low Density Polyethylene (LLDPE) and High-density polyethylene (HDPE).

23. The microcatheter of claim 19 wherein the first and second layers define a line of distinction between the first and second materials.

24. The microcatheter of claim 19 wherein the first layer extends along an entire length of the coupling.

25. The microcatheter of claim 19 wherein the coupling is configured such that an entirety of the first material is disposed proximally of an entirety of the second material.

26. A method of manufacturing a microcatheter, the method comprising:
heating a portion of an elongate flexible tubular body and a portion of a coupling to form a first bond therebetween, the tubular body having a proximal end, a distal end, and at least one lumen extending axially therethrough, and the coupling comprising a first layer and a second layer made from different materials, the first layer being made from a first material and the second layer being made from a second material, wherein the first material is different from the second material; and
heating a portion of a tip body and a portion of the coupling to form a second bond therebetween, wherein the first bond and the second bond have different strengths, the tip body having a proximal end and a distal end and a lumen extending axially therethrough: and
applying a hydrophilic coating to the coupling, to the tubular body and to the tip body, the first material of the coupling being compatible with the hydrophilic coating.

27. The microcatheter of claim 1 wherein the first and second layers define a line of distinction between the first and second materials.

28. The method of claim 26 wherein the first and second layers define a line of distinction between the first and second materials.

* * * * *